United States Patent
Scheuering et al.

(10) Patent No.: US 8,254,653 B2
(45) Date of Patent: Aug. 28, 2012

(54) METHOD FOR VISUALIZING A THREE-DIMENSIONAL IMAGE DATA RECORD FROM AN X-RAY CT EXAMINATION AND WORKSTATION FOR CARRYING OUT THE METHOD

(75) Inventors: Michael Scheuering, Nürnberg (DE); Fernando Vega-Higuera, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1056 days.

(21) Appl. No.: 12/213,744

(22) Filed: Jun. 24, 2008

(65) Prior Publication Data

US 2008/0317318 A1 Dec. 25, 2008

(30) Foreign Application Priority Data

Jun. 25, 2007 (DE) .................. 10 2007 029 159

(51) Int. Cl.
*G06K 9/00* (2006.01)
(52) U.S. Cl. ............................. 382/131; 378/4
(58) Field of Classification Search ............. 378/4–20; 382/128, 131
See application file for complete search history.

(56) References Cited

U.S. PATENT DOCUMENTS

| | | | | |
|---|---|---|---|---|
| 2004/0087850 | A1* | 5/2004 | Okerlund et al. | 600/407 |
| 2005/0041769 | A1* | 2/2005 | Launay et al. | 378/4 |
| 2005/0113679 | A1 | 5/2005 | Suryanarayanan et al. | |
| 2005/0272999 | A1 | 12/2005 | Guendel | |
| 2006/0235288 | A1* | 10/2006 | Lavi | 600/407 |
| 2007/0047792 | A1 | 3/2007 | Scheuering et al. | |

FOREIGN PATENT DOCUMENTS

| | | |
|---|---|---|
| DE | 102004056783 A1 | 6/2005 |
| DE | 102004027709 A1 | 1/2006 |
| DE | 102005039685 A1 | 3/2007 |

OTHER PUBLICATIONS

Leo Grady, Eric L. Schwartz, "Isoperimetric Graph Partitioning for Image Segmentation", IEEE Trans. Pattern Anal. Mach. Intell. 28(3): pp. 469-475 (2006); Others;.
German Office Action issued Jan. 30, 2008.

* cited by examiner

*Primary Examiner* — Hoon Song
(74) *Attorney, Agent, or Firm* — Harness, Dickey & Pierce, P.L.C.

(57) ABSTRACT

A method and a workstation are disclosed for visualizing a three-dimensional image data record having a multiplicity of voxels of a heart of a patient, recorded with the aid of an x-ray CT examination carried out with contrast agent present in the bloodstream. In at least one embodiment, the method includes saving the CT image data record including a multiplicity of voxels defined by absorption values, determining the voxels associated with the chamber of the heart by segmenting the chambers of the heart filled with blood containing the contrast agent, removing the image information from the voxels associated with the chambers of the heart, calculating a two-dimensional virtual projection from the remaining CT image data record, and displaying the virtual two-dimensional projection.

21 Claims, 5 Drawing Sheets

METHOD FOR VISUALIZING A THREE-DIMENSIONAL IMAGE DATA RECORD FROM AN X-RAY CT EXAMINATION AND WORKSTATION FOR CARRYING OUT THE METHOD

PRIORITY STATEMENT

The present application hereby claims priority under 35 U.S.C. §119 on German patent application number DE 10 2007 029 159.2 filed Jun. 25, 2007, the entire contents of which is hereby incorporated herein by reference.

FIELD

Embodiments of the invention generally relate to a method and a workstation for visualizing a three-dimensional image data record having a multiplicity of voxels of a heart of a patient, with the aid of an x-ray CT examination carried out with contrast agent present in the blood stream.

BACKGROUND

It is commonly known to carry out x-ray CT examinations of the heart with contrast agent present. In the case of these examinations, the individual coronary vessels visually stand out due to the presence of contrast agent, with dedicated visualization algorithms being used for better display of these vessels and showing in three dimensions only the vessels filled with contrast agent, without other artifacts. If such segmentation is carried out automatically for all vessels filled with contrast agent, the problem arises that the chambers of the heart, which are surrounded by the coronary vessels, are also segmented, as a result of which the smaller vessels fade into the background and thus their evaluation deteriorates. Although in principle it is possible to individually segment single vessels by manual inputs so that finally a multiplicity of single vessels are segmented without the chambers of the heart, such a method is however firstly very time consuming and secondly there is the risk of overlooking or incorrectly segmenting single vessels, that is to say overestimating or underestimating the vessel size due to the manual operation. A further problem is that such a view of individually displayed segmented vessels does not correspond to the view a cardiologist is used to from cardiac catheter examinations.

SUMMARY

In at least one embodiment of the invention, an automated imaging method is disclosed which leads to a display of coronary arteries as known from cardiac catheter examinations monitored by x-ray imaging.

The inventors have recognized, in at least one embodiment, that a cardiac CT image with contrast agents, displayed in a manner customary to the radiologist, can be generated in a simple manner and automatically by automatically determining the location of the chambers of the heart in the CT volume data of a heart, for example on the basis of the large volume filled with contrast agent, this volume of the chambers of the heart being subsequently segmented and the segmented volume of the chambers of the heart being removed from the CT volume data record. Subsequently, in an established manner, for example by a minimum intensity projection (MIP) or by calculating a transmission image or by volume rendering, a two-dimensional view known to the operator can be generated in which the coronary vessels can be diagnosed in the best possible manner. Additionally, it is possible to remove from the CT data record, which is used to subsequently generate the projection, the bones interfering with a free view of the heart, that is to say it is possible to "peel" the heart out of the thorax, thus allowing a free view of the coronaries.

In accordance with this basic thought, the inventors propose, in at least one embodiment, a method for visualizing a three-dimensional image data record having a multiplicity of voxels of a heart of a patient, recorded with the aid of an x-ray CT examination carried out with contrast agent present in the bloodstream, wherein the following method steps are carried out automatically:

saving the CT image data record comprising a multiplicity of voxels defined by absorption values, determining the voxels associated with the chamber of the heart by segmenting the chambers of the heart filled with blood containing the contrast agent, removing the image information from the voxels associated with the chambers of the heart, calculating a two-dimensional virtual projection from the remaining CT image data record, and displaying the virtual two-dimensional projection.

Hence, at least one embodiment of this method does not involve segmentation of all blood vessels filled with contrast agent; in fact, only a segmentation of the blood volume of the chambers of the heart is carried out and these voxels are subsequently removed from the CT volume data record so that a projection display with this CT volume data can be generated which has only the contrast enhancements of the contrast agent itself. This results in a view which very strongly resembles a normal projective transmission image, created during cardiac catheterization with contrast agents being administered.

It is additionally advantageous if, prior to the projection, voxels which lie outside the heart are removed from the CT image data record. This results in the heart being, so to speak, "peeled" out of the thorax, so that no disturbing shadows from the ribs or the air volume in the lung disturb the findings.

According to at least one embodiment of the invention, the calculation of the projection can be in the form of a generally known minimum intensity projection (MIP) or an inverse MIP. It is also possible to simulate the calculation of the projection in the form of a transmission x-ray image based on the treated CT volume data. Furthermore, it is possible to calculate the projection using the generally known "volume rendering" method.

According to one development of the method according to at least one embodiment of the invention, the inventors furthermore propose that, when marking a vessel in the displayed projection, at least one slice image is displayed which cuts the vessel at the marked location. Here, this can be, for example, an axial, coronal or sagittal slice image. Furthermore, reformatted grayscale slice images can be shown without having to run through the stack of slice images.

In a further embodiment, a slice image which is perpendicular to the direction of the vessel is indicated by marking a point on a coronary vessel so that the cross section of the vessel is shown.

In accordance with the basic idea of at least one embodiment of the previously described method, it is also within the scope of the invention to describe a workstation, preferably of a CT system, comprising at least one processor, memory and computer program code saved therein for imaging CT volume data of a patient, wherein, according to the invention, computer program code should also be contained in the memory which, while the workstation is being used, carries out the method steps of the previously described method according to at least one embodiment of the invention.

BRIEF DESCRIPTION OF THE DRAWINGS

In the following text, embodiments of the invention is described in more detail with the aid of the figures, with only features required to understand the invention being illustrated. In this case, the following reference symbols are used: 1—multi-slice CT system; 2—first x-ray tube; 3—first detector system; 4—second x-ray tube; 5—second detector system; 6—gantry housing; 7—patient; 7.1—heart of the patient; 8—moveable patient couch; 9—system axis; 10—control and calculation unit; 10.1—memory of the control and calculation unit; 11—CT scanning; 12—CT volume data record; 13-18—method steps; 19—virtual projection display; $Prg_1$-$Prg_n$—program code.

In detail.

DETAILED DESCRIPTION OF THE EXAMPLE EMBODIMENTS

Figure 1:
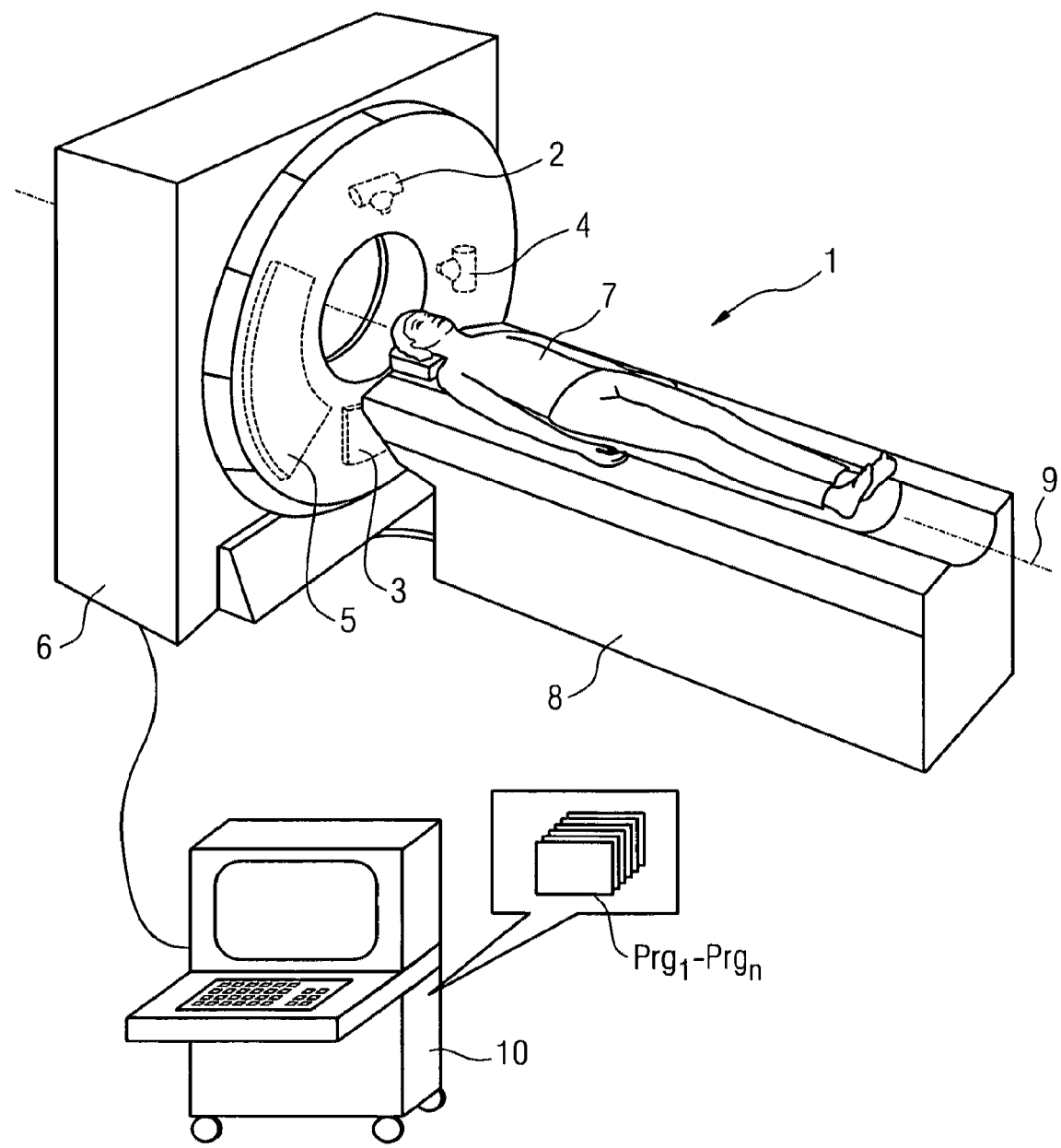
FIG. 1 shows a multi-slice CT scanner.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows a modern multi-slice CT scanner 1 with two focus detector systems, including a first x-ray tube 2 with an opposite detector 3 and a second x-ray tube 4 with an opposite detector 5 and arranged on the gantry, offset at an angle with respect to the first tube. The patient 7 is located on a patient couch 8, which is movable in the direction of the system axis 9, and, during the scanning process, the patient can continuously be pushed through the measurement field of the two x-ray tubes 2 and 4 through the opening in the gantry housing 6, so that a spiral scan is generated. A system such as this is generally controlled by a control and calculating unit 10, which has in its memory 10.1 program code in the form of computer programs $Prg_1$-$Prg_n$ which, during operation, carry out the scanning, reconstruction and imaging. Program code Prg$_x$ which carries out the method according to an embodiment of the invention can also be saved in this memory 10.1.

Figure 2:
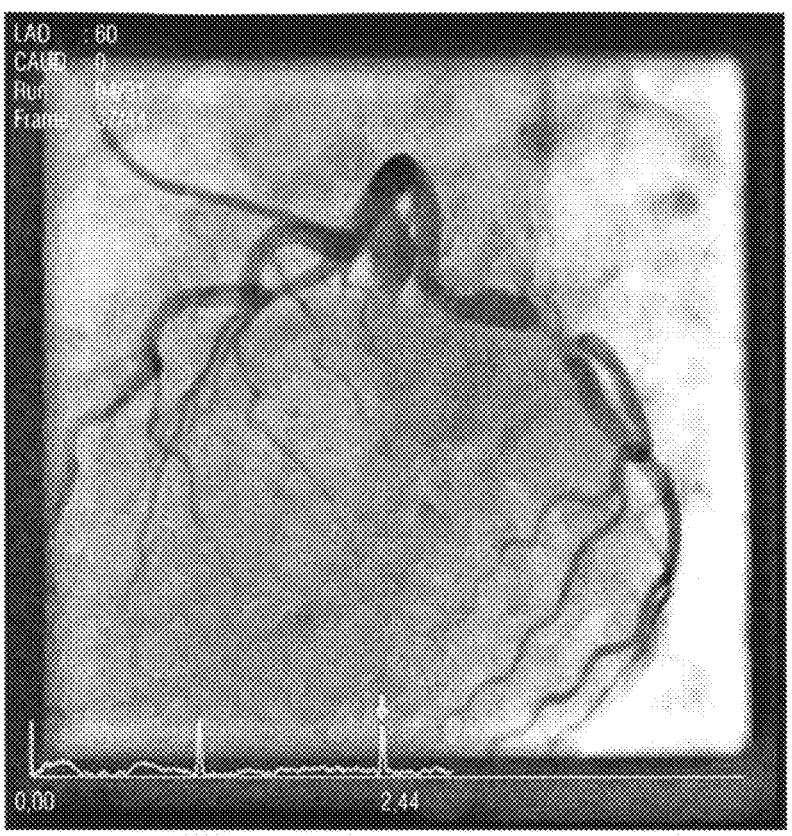
FIG. 2 shows an x-ray transmission image of a cardiac catheter examination using a contrast agent applied by the catheter.
Figure 3:
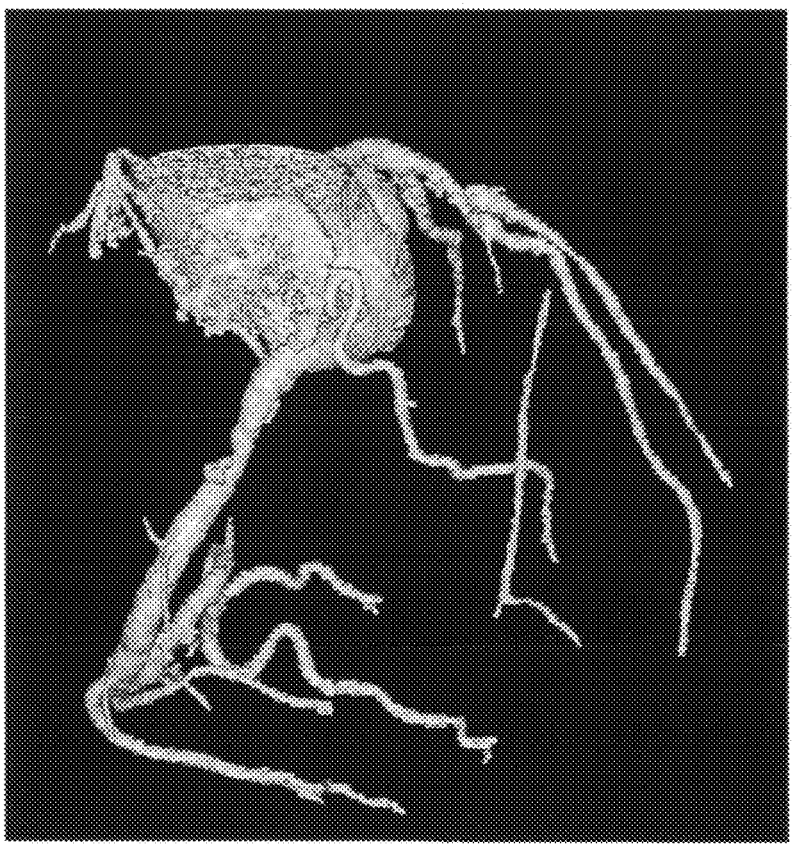
FIG. 3 shows an illustration of manually selected and segmented coronary vessels of a CT volume data record.

Such modern multi-slice CT (MSCT) scanners 1 are capable of, in the field of cardiac analysis, recording an exact anatomical image of the coronary vessels in a short scan time. Using conventional analysis programs the radiologist or cardiologist is able to examine reconstructed 3D-data of the coronary vessels and precisely measure stenotic areas. Usually, the extracted coronary vessels are displayed as shown in FIG. 3. However, it is important for cardiologists to see the recorded CT data and the vessel anatomies contained therein as illustrated in FIG. 2, which is what they are used to. Such displays as shown in FIG. 2 arise from interventional cardiology and are based on the fluoro-illumination using x-ray technology when a catheter is inserted while administering a contrast agent.

In the case of the transmission illustration shown in FIG. 2, an image contrast by way of a contrast agent is generated only in the coronary vessels accessed by the catheter. The contrast agent is also administered only where it is necessary. A "free" view of the coronary vessels is thus possible. However, in the case of an MSCT-examination of the heart using a contrast agent, the contrast agent is not injected by a cardiac catheter; instead, contrast agent is supplied by way of a peripheral venous or arterial access so that all of the blood in the heart—at least in the left half of the heart; this depends on the bolus timing—that is to say the chambers of the heart as well, are filled with blood enhanced with contrast agent. This results in the background of the coronaries being displayed with almost identical absorption values to the coronaries themselves, making it harder to identify the coronaries, and thus being counter-productive.

Figure 4:
FIG. 4 shows multi-planar reformatting (MPR) of an original CT volume data record from a scan with an administered contrast agent.

FIG. 4 shows an image of a longitudinal axis slice of such an MSCT examination through the human heart. In this case, the high absorption values in the left half of the heart and the thus reduced capability to identify the coronaries can clearly be seen.

Figure 5:
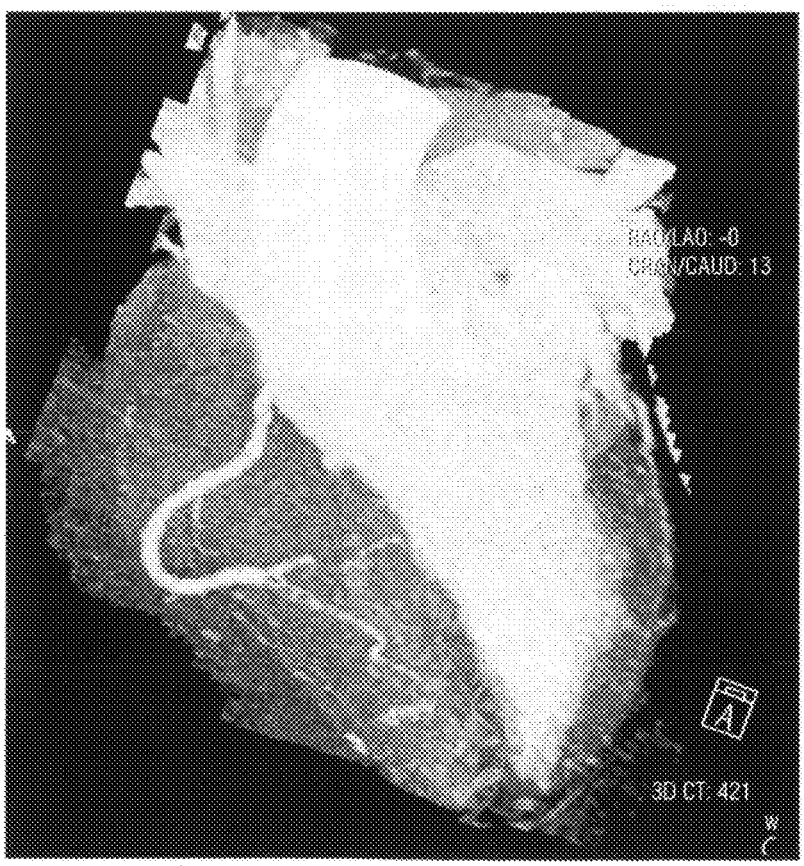
FIG. 5 shows a MIP view of the CT volume data record from FIG. 4.

By way of the established method known as minimum intensity projection (MIP) the view can be improved somewhat, as shown in FIG. 5. However, it is not possible to identify the coronaries in a corresponding manner to a transmission image as shown in FIG. 2.

Until now, a view comparable to FIG. 3 has been achieved only by separating the vessels manually from the remainder of the data record in a three-dimensional MSCT display with the aid of conventional segmentation methods. The segmented volume can subsequently be used as a mask to be subtracted from the remaining volume and then be displayed overall in the form of a MIP or inverted MIP display. However, in this case, the problem often arises that the generation of such an image is very complex, since a large number of user steps which have to be carried out manually are required, such as manually "clicking" on coronaries to be segmented. Furthermore, coronary vessels can be overlooked in this case, and will subsequently not be displayed for the findings.

Figure 6:
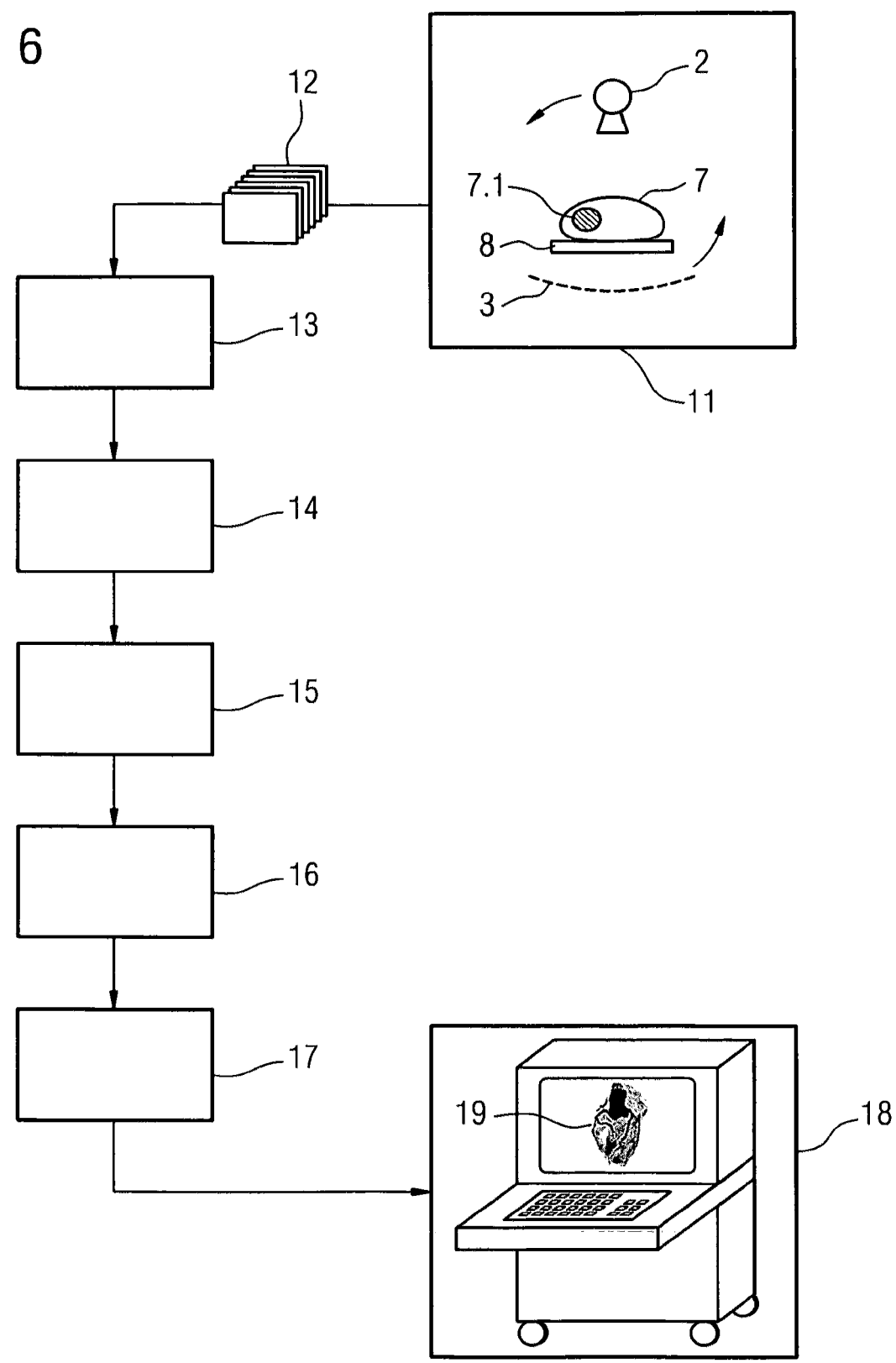
FIG. 6 shows a flowchart of the method according to an embodiment of the invention.

In order to overcome the problems details above, a CT examination 11 is now carried out as illustrated in the flowchart in FIG. 6, and the volume data record 12 comprising a multiplicity of voxels and reconstructed in this way is saved in method step 13. Subsequently, using established image processing methods, the contrasted blood in the chambers of the heart is automatically segmented according to method step 14 and removed from the volume data record 12 according to method step 15. With regard to these established methods, reference is made for example to the document Leo Grady, Eric L. Schwartz, "Isoperimetric Graph Partitioning for Image Segmentation", *IEEE Trans. Pattern Anal. Mach. Intell.* 28(3): 469-475 (2006). This method permits automatic identification of the heart, segmentation of its heart chambers and their subsequent removal. Finally, in method step 16, a virtual projection 19 of the volume data onto a plane is calculated from the CT volume data record 12 processed in this way, and is displayed in method step 17.

Figure 7:
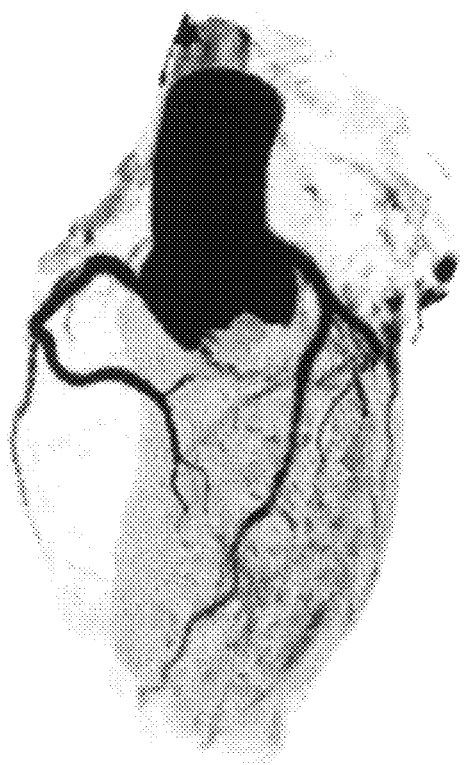
FIG. 7 shows a MIP view of a CT volume data record processed according to an embodiment of the invention.
Figure 8:
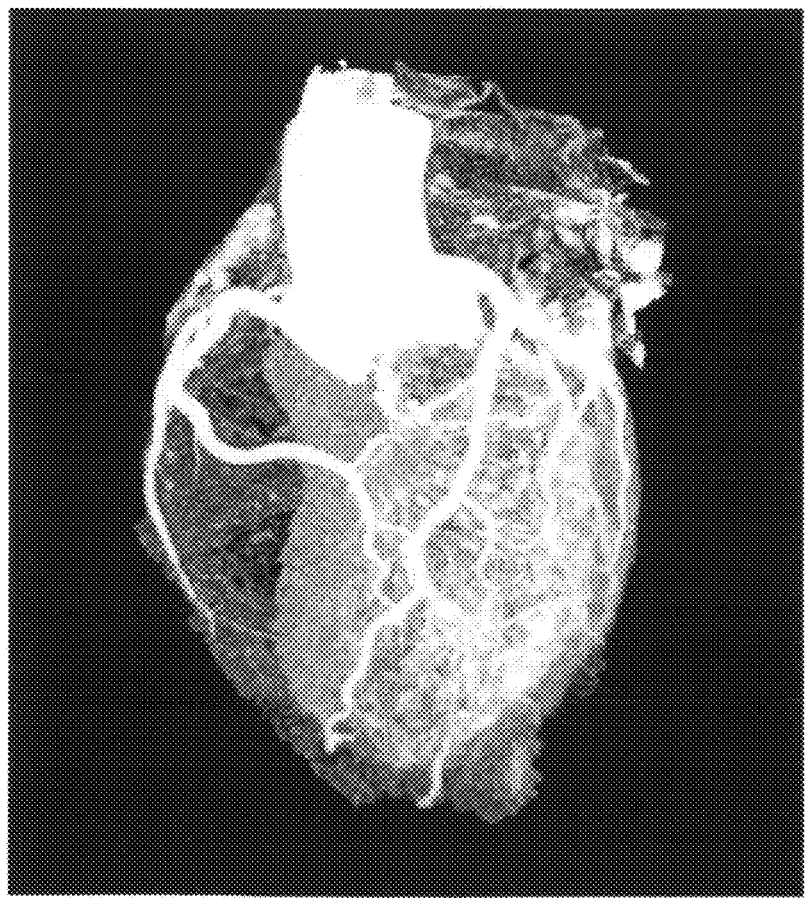
FIG. 8 shows an inverted MIP view of a CT volume data record processed according to an embodiment of the invention.

It is thus possible to generate, without any user interaction, images as shown in FIGS. 7 and 8 from CT volume data records of a cardiac scan using contrast agents. FIG. 7 shows an MIP view, whereas FIG. 8 shows an inverted MIP view. These illustrations correspond to the customary display of a cardiac catheter examination using x-ray illumination. In addition, in this illustration it is likewise possible to remove the entire heart from the thorax. The view can also be rotated freely in space for better viewing and translations can be carried out; furthermore it is possible to zoom into and out of the view. Thus, a free and optimum view of the coronaries is ensured without disturbing the blood in the chambers of the heart or in the surrounding bone or cartilage tissue or in the peripheral vessels. In addition, in this display, the modeled aorta is shown as an aorta-stump with valve-modeling.

Using this method, faster findings of the entire cardiological volume data record are possible. The total clinical workflow of the findings can thus be significantly speeded up. In particular, coronary anomalies, stenoses, calcifications and occlusions can be recognized more easily, at a glance, using the method according to an embodiment of the invention.

In addition, it is now possible by simply clicking on emphasized coronaries to obtain a direct relationship with the axial, sagittal, coronal or reformatted grayscale slice images, which additionally can be displayed without having to run through the stack of slice images.

An additional advantage of an embodiment of the above-mentioned method compared to conventional catheter examinations is that the actual vessel anato my does not have to be touched for the display, that is to say no invasive procedure is necessary. As described above, cardiologists and radiologists were forced until now to separate the coronaries from the remaining volume using segmentation methods. However, this carries the risk that imprecise or even wrong segmentations lead to misinterpretation of the symptoms of the patient by the medical practitioner. If the blood in the chambers of the heart is only virtually removed without touching the coronaries, this cannot occur.

It is self-evident that the previously mentioned features of the invention can be used not only in the respectively mentioned combination, but also in different combinations or on their own without leaving the scope of the invention.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for displaying a virtual two-dimensional projection, the method comprising:
    saving a CT image data record including a multiplicity of voxels of a heart of a patient, recorded with the aid of an x-ray CT examination carried out with contrast agent present in a bloodstream, defined by absorption values;
    determining voxels associated with a chamber of the heart by segmenting the chambers of the heart filled with blood containing the contrast agent;
    removing image information from the voxels associated with the chambers of the heart;
    calculating the two-dimensional virtual projection from the remaining CT image data record; and
    displaying the virtual two-dimensional projection.

2. The method as claimed in claim 1, wherein, prior to calculating the projection, voxels which lie outside of the heart are removed from the CT image data record.

3. The method as claimed in claim 1, wherein the calculation of the projection is in the form of a minimum intensity projection.

4. The method as claimed in claim 1, wherein the calculation of the projection is in the form of an inverted minimum intensity projection.

5. The method as claimed in claim 1, wherein the calculation of the projection is simulated by a transmission x-ray image.

6. The method as claimed in claim 1, wherein the calculation of the projection is carried out by volume rendering.

7. The method as claimed in claim 1, wherein, when a vessel is marked in the displayed projection, at least one slice image is displayed which cuts the vessel at the marked point.

8. The method as claimed in claim 7, wherein at least one axial slice image is shown as a slice image.

9. The method as claimed in claim 7, wherein at least one sagittal slice image is shown as a slice image.

10. The method as claimed in claim 7, wherein at least one coronal slice image is shown as a slice image.

11. The method as claimed in claim 7, wherein a slice image perpendicular to the direction of the vessel is shown as a slice image.

12. A workstation, comprising:
    at least one processor; and
    at least one memory including computer program code stored therein for imaging CT volume data of a patient, and for carrying out the method of claim 1 when executed by the at least one processor during use of the workstation.

13. The method as claimed in claim 2, wherein the calculation of the projection is in the form of a minimum intensity projection.

14. The method as claimed in claim 2, wherein the calculation of the projection is in the form of an inverted minimum intensity projection.

15. The method as claimed in claim 2, wherein the calculation of the projection is simulated by a transmission x-ray image.

16. The method as claimed in claim 2, wherein the calculation of the projection is carried out by volume rendering.

17. The method as claimed in claim 2, wherein, when a vessel is marked in the displayed projection, at least one slice image is displayed which cuts the vessel at the marked point.

18. The method as claimed in claim 17, wherein at least one axial slice image is shown as a slice image.

19. The method as claimed in claim 8, wherein at least one sagittal slice image is shown as a slice image.

20. The method of claim 1, wherein at least one of the saving, determining, removing, calculating and displaying are performed automatically.

21. A non-transitory computer readable medium including program segments for, when executed on a computer device, causing the computer device to implement the method of claim 1.

* * * * *